United States Patent [19]

Moa et al.

[11] Patent Number: 5,193,532
[45] Date of Patent: Mar. 16, 1993

[54] DEVICE FOR GENERATING BY MEANS OF EJECTOR ACTION A CONTINUOUS POSITIVE AIRWAY PRESSURE (CPAP) DURING SPONTANEOUS BREATHING

[76] Inventors: Conny P. G. Moa, Stenåldersvägen 22, S-831 61 Östersund; Kjell O. Nilsson, Bangårdsgatan 71, S-831 45 Östersund, both of Sweden

[21] Appl. No.: 687,923
[22] PCT Filed: Dec. 6, 1989
[86] PCT No.: PCT/SE89/00715
§ 371 Date: Jul. 23, 1991
§ 102(e) Date: Jul. 23, 1991
[87] PCT Pub. No.: WO90/06149
PCT Pub. Date: Jun. 14, 1990

[30] Foreign Application Priority Data
Dec. 6, 1988 [SE] Sweden .................. 8804404

[51] Int. Cl.⁵ ............................................. A61M 16/00
[52] U.S. Cl. ................... 128/204.25; 128/912; 128/204.18
[58] Field of Search ............. 128/204.18, 204.25, 128/205.11, 912

[56] References Cited

U.S. PATENT DOCUMENTS

| | | | |
|---|---|---|---|
| 2,985,357 | 5/1961 | Carolan | 128/204.25 |
| 3,630,196 | 12/1971 | Bird | 128/204.25 |
| 4,098,290 | 7/1978 | Glenn | 128/204.25 |
| 4,261,355 | 4/1981 | Glazener | 128/204.25 |
| 4,282,869 | 8/1981 | Zidulka | 128/204.25 |
| 4,495,946 | 1/1985 | Lemer | 128/204.25 |
| 4,537,188 | 8/1985 | Phuc | 128/204.25 |
| 4,681,100 | 7/1987 | Brychta et al. | 128/204.25 |
| 4,796,617 | 1/1989 | Matthews et al. | 128/205.11 |
| 5,000,173 | 3/1991 | Zalkin et al. | 128/204.25 |

FOREIGN PATENT DOCUMENTS

3119814 7/1984 Fed. Rep. of Germany .

Primary Examiner—Edgar S. Burr
Assistant Examiner—Aaron J. Lewis
Attorney, Agent, or Firm—Young & Thompson

[57] ABSTRACT

A device for generating by ejector action a continuous positive airway pressure (CPAP), comprising a breathing-channel which at one end opens into the atmosphere and at another end is adapted to be provided with an attachment device to the nose and/or mouth of the patient. An inlet channel is connected with the breathing-channel at a point between its ends for fresh gas, the flow of which may be adjusted to obtain an adjustable positive pressure within the breathing-channel. The breathing channel (10) has a first branch-channel (11) which is connectable to the attachment device and a second branch-channel (12) which opens into the atmosphere, the two branch-channels together forming an acute angle (A) of 30°–50° with each other. The inlet channel (13) is situated in the extension of the first branch-channel (11) and is connected to the second branch-channel (12) in such a manner that the stream of fresh gas is directed mainly co-axially into the first branch-channel, producing an ejector action.

2 Claims, 1 Drawing Sheet

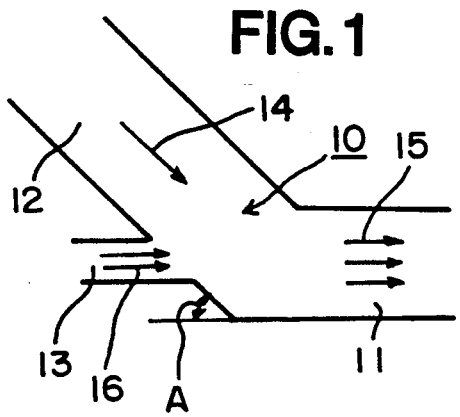
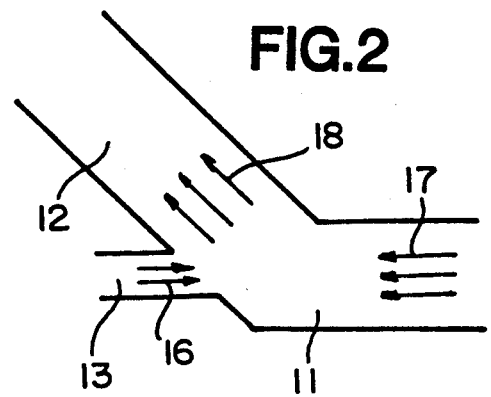
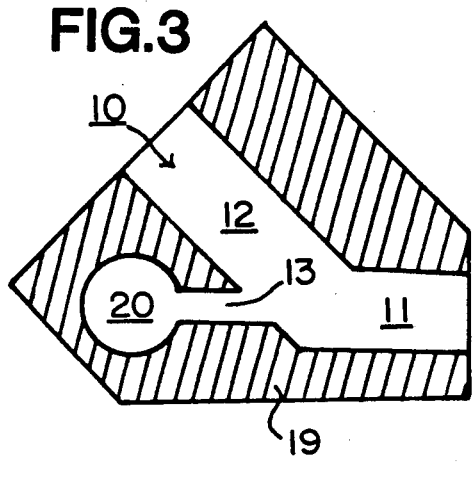
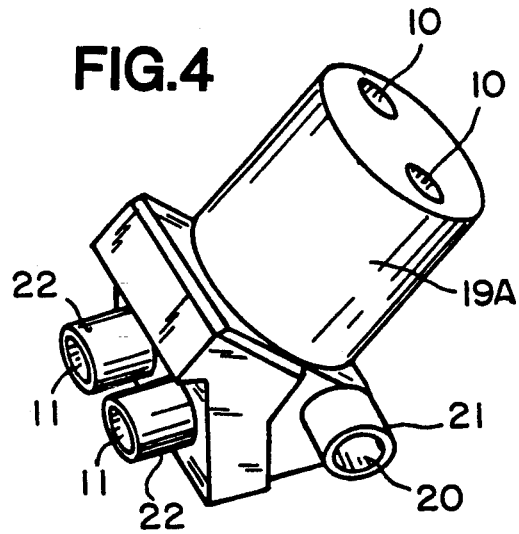
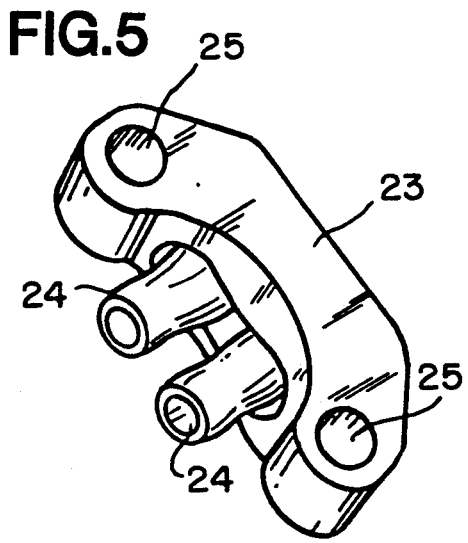
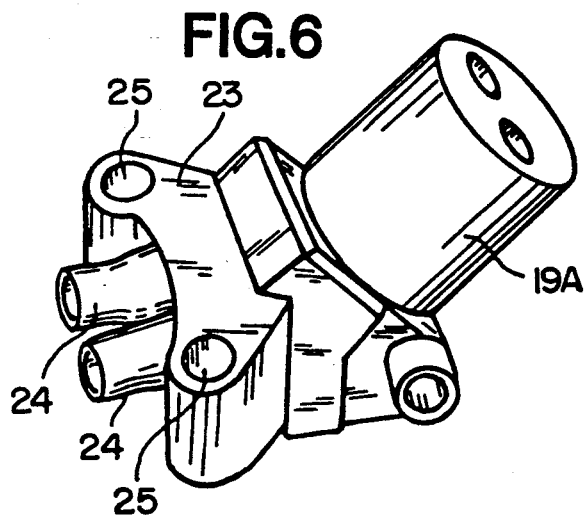

DEVICE FOR GENERATING BY MEANS OF EJECTOR ACTION A CONTINUOUS POSITIVE AIRWAY PRESSURE (CPAP) DURING SPONTANEOUS BREATHING

The present invention relates to devices used to improve gas exchange during spontaneous breathing when the patient's ability to breathe is impaired. The device is of the type which comprises a breathing-channel which at its one end opens into the atmosphere and at its other end has an attachment means for connection to a patient's airway via the nose and/or mouth. Further, the device has an inlet or fresh-gas channel which is connected with the breathing-channel at a point between its ends and allows the flow of the flesh gas to be adjusted to obtain an adjustable positive pressure within the breathing-channel.

The principle involved in such a device is that the patient breathes against a pressure above atmospheric pressure, which facilitates spontaneous breathing in certain conditions of impaired pulmonary function. With hitherto well-known devices of this type of simple and thereby inexpensive design, the breathing-channel consists of relatively long tubing, which in turn results in relatively long columns of air. When the patient breathes in, the pressure then tends to fall in the breathing-channel. In order to attain the best possible breathing conditions, however, the pressure in the patient's airway should be as constant as possible during the breathing cycle. Up until now this has been difficult to achieve, even with the well-known devices which are relatively complicated in that they work with movable valves and electronic components. This is particularly true of systems connected via the nose.

The purpose of the present invention is therefore to provide a device of the type under consideration which, while retaining its simplicity, makes it possible to sustain a positive airway pressure with minimal pressure variations and which can thereby replace also the more complicated and relatively expensive well-known devices as well. This is achieved with a device which according to the invention is characterized by the fact that the breathing-channel consists of a first branch-channel which fits into the attachment means and by a second branch-channel, which opens into the atmosphere, the two branch-channels forming an angle with one another.

The fresh-gas channel is situated substantially in the extension of the first branch-channel and is connected to the second branch-channel in a way that causes the stream of fresh-gas to be directed mainly co-axial into the first branch-channel. Each branch-channel's cross-sectional area is several times greater than the smallest cross-sectional area of the inlet channel and the length of each branch-channel is relatively short in that the length is preferably a maximum of five times its inner diameter. In addition, the breathing-channel is built together with the inlet channel into a compact unit which can be secured to the patient's nose and/or mouth by means of a strap, band or ribbon.

Thanks to the particular way in which the inlet channel is attached to the angled breathing-channel, an ejector action is attained in an extremely simple manner which, depending on the size of the fresh-gas flow, generates the desired pressure (CPAP) in the first branch-channel which is connected directly to the patient's airway.

The ejector action counteracts the tendency to decreasing pressure during the inspiration phase, in that breathing-gas and/or atmospheric air is sucked in from the other branch-channel. During the expiration phase the tendency to increasing in pressure is counteracted by the breathing-channel's cross-sectional area, which is several times greater than that of the inlet channel, which allows the expiratory air to be added to the fresh-gas flow without the pressure gradient in the system being appreciably affected. The pressure thereby tends to be constant at constant gas flows, despite variations in the breathing-channel during the breathing cycle.

The device according to the invention thus forms a compact unit in which the air columns in the branch-channels are relatively short in order to avoid backlogs in the gas supply when the pressure tends to fall in the first branch-channel during the inspiration phase.

The compact unit made possible according to the invention can be manufactured in plastic in a simple and inexpensive way. Since it is light in weight, it will not bother the patient when it is secured to his nose or mouth. The unit does not require any moving parts. The only tubing necessary is a relatively slender hose for supplying fresh-gas to the fresh-gas inlet channel.

Some embodiments of the invention are shown in the attached drawings.

FIG. 1 is a schematic sectional view through the device with stream arrows indicating the inspiration phase.

FIG. 2 is the same sectional view with stream arrows indicating the expiration phase.

FIG. 3 is an enlarged schematic sectional view through a body of plastic material, in which the required channels are provided.

FIG. 4 is a schematic picture in perspective to the device intended especially for newborn infants.

FIG. 5 is a schematic picture in perspective of an attachment with two nasal attachment tubes by which the attachment can be fastened onto the two connection tubes of the device in FIG. 4.

FIG. 6 is a schematic picture in perspective of the attachment in FIG. 5 mounted on the device in FIG. 4.

FIG. 1 shows diagrammatically a breathing-channel 10 which is angled and thereby divided into a first branch-channel 11, which can be attached to the patient's nose and/or mouth and a second branch-channel 12 which opens to the free atmosphere. The angle A between the channels is 45° in the example shown and is preferably in the area of 30°-50°.

In the extension of the first branch-channel and essentially co-axially is an inlet channel 13 for fresh gas. This channel has a several times smaller area than that of channels 11 and 12. The inlet channel is connected to the second branch-channel 12 and thus directs the stream of fresh-gas essentially co-axially into the first branch-channel. By means of the angled arrangement of the breathing-channel and the special attachment of the inlet channel and the relation between the cross-sectional areas of the inlet channel and the branch-channel, a desired jet entrainment is attained in a simple manner. The atmospheric air and/or excess fresh-gas indicated by arrow 14 can thus be sucked into channel 11 during the inspiration phase so that the pressure in the airway of the patient tends to be maintained, even if the inspiratory flow exceeds the fresh-gas flow. Arrows 15 indicate the flow to the lungs and arrows 16 indicate the outflow from the inlet channel 13. At a maximum inspiratory flow the ejection flow 16 will consequently bring gas from channel 12 with it, thereby counteracting a lowering of pressure in the airway of the patient.

During the expiratory phase according to FIG. 2, the expired gas according to arrows 17 together with the excess gas flow are directed out through branch channel 12 as indicated by arrows 18. Since branch channel 12 has a relatively large flow capacity, a rise over the desired value in elevated pressure in the airway of the patient is counteracted.

FIG. 3 is a sectional view of a body of plastic material 19, in which the channels 11, 12, 13 in question are provided. The inlet channel 13 branches out from a supply channel 20. Usually two systems of channels 11, 12 and 13 are situated next to each other in the plastic body, and channels 11 can each be attached to a nostril, especially in the case of newborn infants.

With tests using an attachment for newborn infants, the channels had the following inner diameters. Channel 11 had a diameter of 3.5 mm, channel 12 had a diameter of 4.0 mm and channel 13 had a diameter of 1.3 mm. Body 19 is consequently relatively small and light so that it can rest comfortably against the patient's face.

Channels 11 and 12 are relatively short in length, preferably five times their diameter at the most.

FIG. 4 shows an embodiment in which the plastic body 19A has two parallel systems of channels 11, 12 and 13 as in FIG. 3. Channel 20 has a connection tube 21 for attachment of a hose for fresh-gas supply. Channels 11 have two connection tubes 22 to which the attachment 23 in FIG. 5 can be fastened.

The attachment 23 has two small prong-like tubes 24 of elastic material. These tubes can be placed in the patient's nose. In turn, these tubes can be attached to tubes 22 in order to fasten the attachment 23 to the plastic body 29A to form the unit shown in FIG. 6. The attachment has two holes 25 for a strip, band or ribbon to be used for holding the attachment in place.

We claim:

1. A device for generating by means of ejector action a continuous positive airway pressure (CPAP) comprising a breathing-channel which at one end opens into the atmosphere and at another end is adapted to be provided with an attachment device to the nose and/or mouth of the patient, and an inlet channel which is connected with the breathing-channel at a point between its ends for fresh gas, the flow of which may be adjusted to obtain an adjustable positive pressure within the breathing-channel, wherein the breathing channel (10) comprises a first branch-channel (11) which is connectable to the attachment device and a second branch-channel (12) which opens into the atmosphere, the two branch-channels together forming an acute angle (A) of 30°-50° with each other, the inlet channel (13) being situated substantially in the extension of the first branch-channel (11) and being connected to the second branch-channel (12) in such a manner that the stream of fresh gas is directed mainly co-axially into the first branch-channel, producing an ejector action, and the cross-sectional area of the respective branch-channel being several times greater than the smallest cross-sectional area of the inlet channel, the inlet channel (13) opening into said breathing channel (10) flush with the side walls of said breathing channel (10).

2. A device according to claim 1, intended to be attached to the nostrils of the patient, wherein the unit includes two parallel breathing-channels (10, 10), each having means (24) for connection to one nostril each, and a channel for the supply of fresh-gas (20) that is branched into two inlet channels (13, 13), connected to the two breathing-channels. i

* * * * *